United States Patent [19]

Vanderwerff

[11] Patent Number: 4,458,047
[45] Date of Patent: Jul. 3, 1984

[54] PROCESS FOR MAKING NAPHTHALENE HYDRODIMER MIXTURES, PRODUCT MIXTURES MADE THEREBY AND THEIR USE AS A PLASTICIZER

[75] Inventor: William D. Vanderwerff, West Chester, Pa.

[73] Assignee: Sun Tech, Inc., Philadelphia, Pa.

[21] Appl. No.: 385,957

[22] Filed: Jun. 7, 1982

[51] Int. Cl.$^3$ .................................................. C08K 5/01
[52] U.S. Cl. ..................................... 524/476; 524/485; 585/410; 585/425
[58] Field of Search .................. 524/476, 477, 485; 585/410, 425

[56] References Cited

U.S. PATENT DOCUMENTS

| | | | |
|---|---|---|---|
| 2,067,316 | 7/1937 | Gray | 524/476 |
| 2,289,743 | 7/1942 | Warner et al. | 524/476 |
| 2,328,633 | 9/1943 | Evans | 524/485 |
| 2,477,717 | 8/1949 | Brandt | 524/485 |
| 3,311,669 | 3/1967 | Bushick | 585/425 |
| 3,336,407 | 8/1967 | Bushick | 260/668 |
| 3,897,374 | 7/1975 | Takahashi et al. | 524/476 |
| 4,219,689 | 8/1980 | Murtha | 585/425 |

FOREIGN PATENT DOCUMENTS

| | | | |
|---|---|---|---|
| 507247 | 11/1954 | Canada | 524/476 |
| 2461472 | 7/1975 | Fed. Rep. of Germany | 524/477 |
| 47-27967 | 10/1972 | Japan | 585/410 |

OTHER PUBLICATIONS

Chemistry of Organic Compounds by Noller, pp. 556-559.

Primary Examiner—Joseph L. Schofer
Assistant Examiner—N. Sarofim
Attorney, Agent, or Firm—J. Edward Hess; Donald R. Johnson

[57] ABSTRACT

A novel process for making novel naphthalene hydrodimer mixtures which contain PTB in varying amounts and have improved plasticizing properties over PTB alone. The improved plasticizing composition is prepared by contacting a mixture of a hydronaphthalene (e.g., tetralin or an alkyltetralin) and naphthalene or an alkylnaphthalene with a strong acid catalyst. Another embodiment of the invention is the plasticized composition.

16 Claims, 6 Drawing Figures

MAJOR-NAPHTHALENE HYDRODIMER TYPES $C_{20}H_{28}$  1,1',2,2',3,3',4,4',5',6',7',8'-DODECAHYDRO-1,2'-BINAPHTHYL $C_{20}H_{24}$  1-PHENYL-4-(5,6,7,8-TETRAHYDRO-2-NAPHTHYL)-BUTANE $C_{20}H_{22}$  1,2,3,4,5',6',7',8'-OCTAHYDRO-2,2'-BINAPHTHYL (A BITETRALYL)

$C_{20}H_{22}$  1-PHENYL-1,2,3,4,5,6,7,8-OCTAHYDROANTHRACENE $C_{20}H_{20}$  1-PHENYL-4-(1-NAPHTHYL) BUTANE $C_{20}H_{18}$  1,2,3,4-TETRAHYDRO-1,1'-BINAPHTHYL $C_{20}H_{18}$  1-PHENYL-5,6,7,8-TETRAHYDROPHENANTHRENE $C_{20}H_{14}$  2,2'-BINAPHTHYL $C_{20}H_{12}$  PERYLENE

SECONDARY NAPHTHALENE HYDRODIMER TYPES $C_{24}$ $C_{28}$ $C_{30}$

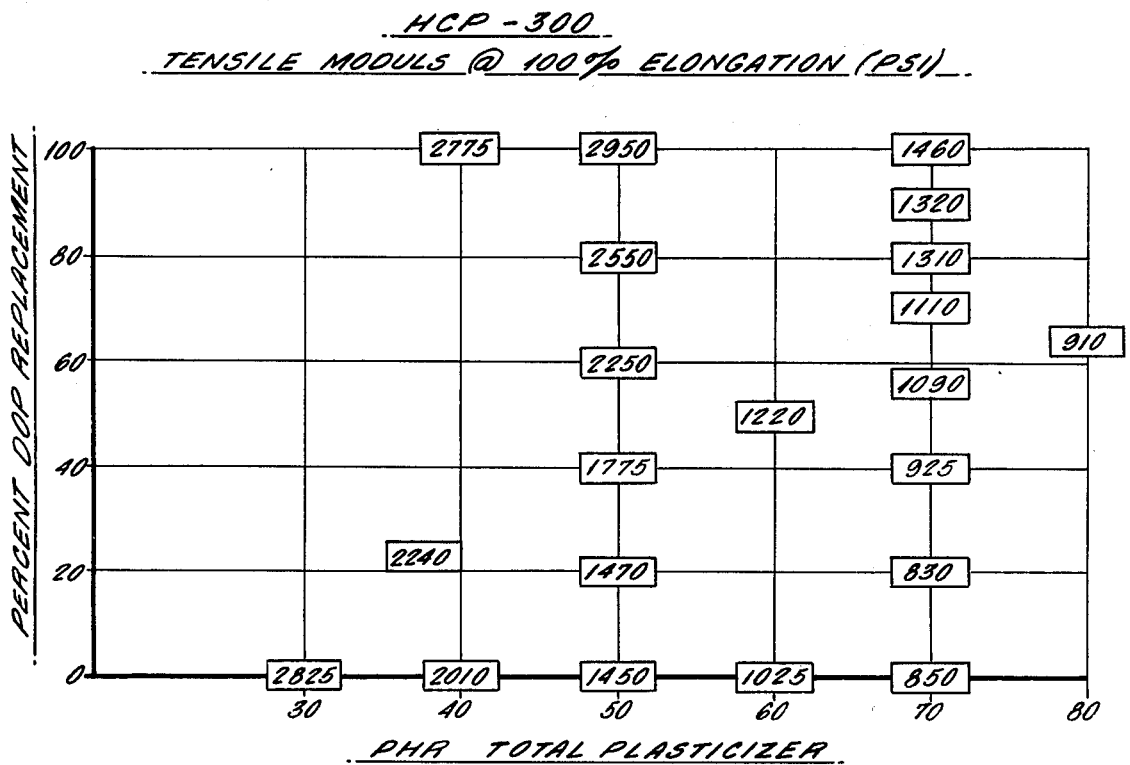
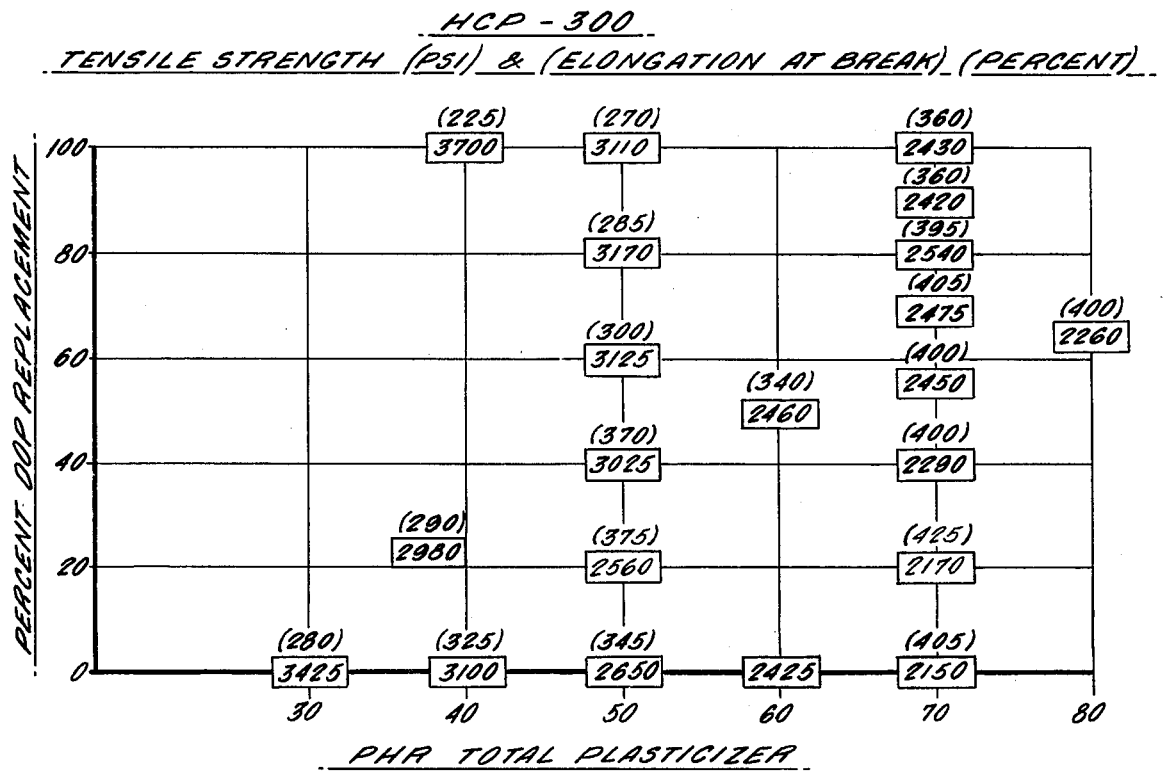

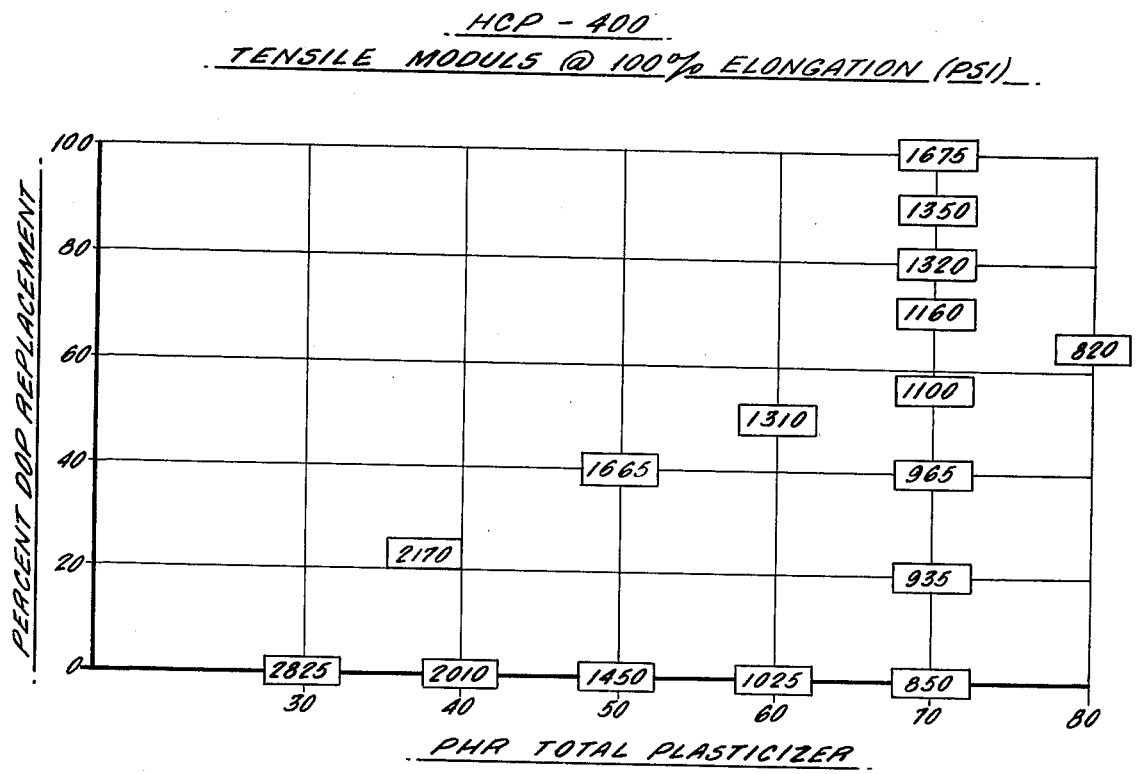
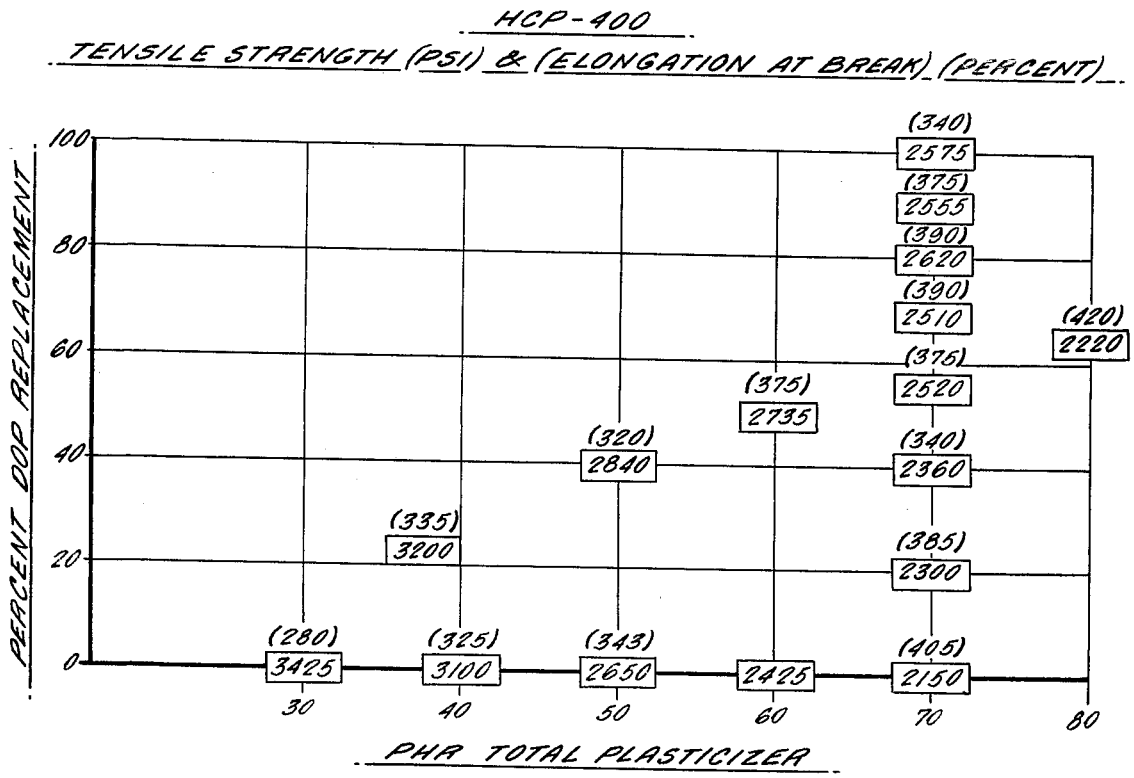

PROCESS FOR MAKING NAPHTHALENE HYDRODIMER MIXTURES, PRODUCT MIXTURES MADE THEREBY AND THEIR USE AS A PLASTICIZER

BACKGROUND OF THE INVENTION

1-Phenyl-4-(2-tetraly)butane and 1-phenyl-4(1-tetralyl)butane, both known as PTB, are known compounds which are obtained by treating 1,2,3,4-tetrahydronaphthalene (tetralin) with a strong acid catalyst:

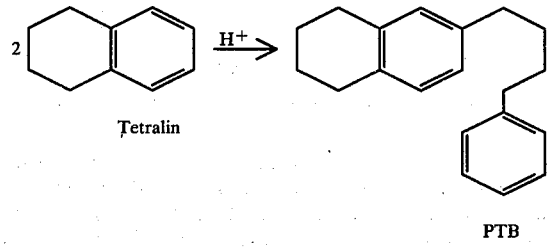

This reaction is discussed in Ber. 57B, 1990 (1924) and in U.S. Pat. No. 3,336,407 where it is pointed out that not only PTB, but other reaction products as well, such as sym-octahydroanthracene (OHA) and sym-octahydrophenanthrene (OHP) are formed. OHA and OHP are known to be plasticizers for polystyrene (U.S. Pat. No. 2,289,743 and U.S. Pat. No. 2,454,851) but, because of their high volatility they would be of little value for most plasticizer applications in polyvinylchloride (PVC) resins due to unacceptably low levels of permanence resulting from evaporative losses. Also obtained in this reaction is some small amount of 2,6-bitetralyl along with minor amounts of other products. Other related art discussing such reactions is includes L. I. Smith and C. Lo. *J. Am. Chem. Soc.* 70., 2209 (1948) and U.S. Pat. No. 3,336,407 (1967).

PTB has been found to be an effective plasticizer for polyvinylchloride (PVC) resins and such use is the subject matter of U.S. Ser. No. 385,958 filed of even date herewith.

BRIEF STATEMENT OF INVENTION

This invention relates to a novel process for making naphthalene hydrodimer mixtures which may contain PTB in varying amounts, and, unexpectedly, have improved plasticizing properties. This improved plasticizing composition is an embodiment of the invention and is prepared readily by contacting a mixture of a hydronaphthalene (e.g., tetralin or an alkyltetralin) and naphthalene or an alkylnaphthalene with a strong acid catalyst. Another embodiment of the invention is the plasticized composition.

BRIEF DESCRIPTION OF DRAWINGS

FIG. 3 and FIG. 4 are graphic displays of data obtained.

FIG. 5 and FIG. 6 are graphic displays of data similar in nature to FIG. 3 and FIG. 4, but for a different naphthalene hydrodimer within the scope of the invention.

DETAILED DESCRIPTION OF THE INVENTION

Figure 1:
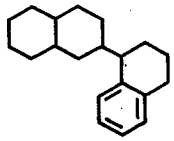
FIG. 1 lists structures for the major naphthalene hydrodimer types.
Figure 1:
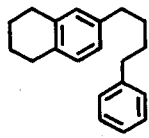
Figure 1:
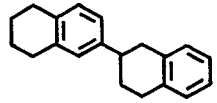
Figure 1:
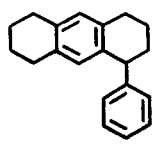
Figure 1:
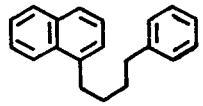
Figure 1:
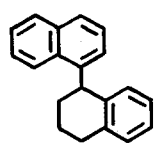
Figure 1:
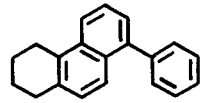
Figure 1:
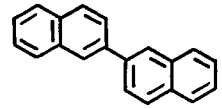
Figure 1:
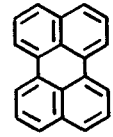

The preferred hydronaphthalenes useful in the invention are tetralin and tetrahydroalkylnaphthalenes such as 5,6,7,8-tetrahydro-2-methylnaphthalene and 1,2,3,4-tetrahydro-1-methyl-6-ethylnaphthalene, for example.

The other component may, as indicated, be naphthalene or an alkylnaphthalene such as 1-methylnaphthalene, 2,3-diethylnaphthalene and the like. A preferred source of such naphthalenes is the complex mixture of methylnaphthalenes from certain petroleum refinery streams. A still more preferred feedstock can be produced from naphthalene, an alkylnaphthalene or an alkylaromatic petroleum refinery stream high in methyl- and dimethylnaphthalenes by partial hydrogenation so as to produce a mixture of alkyltetralins and alkylnaphthalenes. Alkylbiphenyls and alkylindans, frequently present in mixed methylnaphthalenes petroleum refinery products, may be present and are not necessary undesirable. The feedstock can, of course, be a mixture of two pure hydrocarbons as for example: tetralin plus naphthalene, tetralin plus 1-methylnaphthalene, or 5,6,7,8-tetrahydro-2-methyl-naphthalene and 1-methyl-2-ethylnaphthalene. As is evident from the above, the alkyl substituent on the tetralin or naphthalene rings will be a lower alkyl group.

Catalysts which may be used for this reaction include Bronsted acids such as HF and especially HF/BF$_3$ mixtures; Lewis acids such as AlCl$_3$ and AlCl$_3$/HCl mixtures and solid catalysts such as acidic "Y" type or any of the more acidic types of the Mobil ZSM series of synthetic shape-selective zeolites. Other strong acid catalysts may be used such as those which are effective for transalkylation reactions such as the commercially significant transalkylation of diethylbenzene with benzene to yield ethylbenzene. An alumina-BF$_3$ catalyst is useful for such transalkylation. Because hydrogen transfer processes play a significant role in the process of this invention, dual-function catalysts may be preferred. By dual-function catalysts is meant catalysts which combine high acidity with hydrogenation capability; for example: platinum on alumina, palladium on acidic "Y" type synthetic zeolite, nickel on silica-alumina and the like. Zeolite type catalysts are preferred for the reaction.

The products obtained by the above described reaction are always naphthalene hydrodimer mixtures even when pure feedstocks are used, as can be seen in Table I. By the term naphthalene hydrodimer we mean any C$_{20}$ hydrocarbon which can formally be considered a dimer of naphthalene but which contains a higher hydrogen to carbon ratio than naphthalene (C$_{10}$H$_8$). Because of the extensive hydrogen transfer activity which is characteristic of the process of this invention, the actual naphthalene hydrodimer mixtures produced may also contain minor amounts of naphthalene dimers (C$_{20}$H$_{16}$), such as phenyltetrahydrophenanthrene, and naphthalene dehydrodimers, such as binaphthyl (C$_{20}$H$_{14}$) and perylene (C$_{20}$H$_{14}$) The primary naphthalene hydrodimers are also subject to a variety of secondary reactions such as isomerization, transalkylation, hydrogen transfer, cyclization, disproportionation, and the like, which can lead to the formation of C$_{18}$, C$_{24}$, C$_{28}$, and C$_{30}$ hydrocarbons (also with varying hydrogen to carbon ratios). FIGS. I and II provide a partial list of the types of naphthalene hydrodimers and associated secondary products which characterize the "naphthalene hydrodimer mixtures" produced by the process of this invention.

and/or alkyltetralins yield quite complex product mixtures.

TABLE I

COMPOSITION OF HYDRODIMER FRACTION OF PRODUCT OF REACTION OF TETRALIN WITH VARIOUS AROMATIC SUBSTRATES AT 125° C. WITH 2 WT. PERCENT AlCl3 (IN WEIGHT PERCENT OF INDIVIDUAL COMPONENT TYPE BY MASS SPECTROSCOPY).

| | | Aromatic Substrate | | | | | |
|---|---|---|---|---|---|---|---|
| Hydrodimer Type | Emperical Formula of Unmethylated Parent Hydrocarbon | Tetralin Alone | Naphthalene | 1-Methyl-naphthalene | 2-Methyl-naphthalene | Refinery Stream "A" (80% Methyl-naphthalenes) | Refinery Stream "B" (50) Methyl-naphthalenes) |
| Phenyltetralylbutane | $C_{20}H_{24}$ | 66.0 | 4.5 | 4.3 | 4.5 | 3.2 | 4.8 |
| Bitetralyl | $C_{20}H_{22}$ | 23.2 | 6.6 | 7.0 | 8.2 | 4.1 | 5.8 |
| Phenylnaphthylbutane | $C_{20}H_{20}$ | 2.4 | 30.6 | 24.0 | 27.0 | 20.1 | 24.3 |
| Tetrahydrobinaphthyl | $C_{20}H_{18}$ | 2.4 | 50.7 | 51.9 | 53.0 | 49.3 | 49.0 |
| Tetrahydroperylene | $C_{20}H_{16}$ | 3.6 | 2.1 | 3.2 | 2.5 | 3.5 | 7.8 |
| Binaphthyl | $C_{20}H_{14}$ | — | 2.4 | 5.1 | 2.3 | 3.0 | 6.2 |
| Perylene | $C_{20}H_{12}$ | 2.4 | 3.1 | 4.5 | 2.5 | 3.8 | 2.1 |

In accord with the present invention, when a mixture of naphthalene and tetralin are contacted with a sufficiently strong acid catalyst a decidedly different reaction sequence predominates that when tetralin alone is so treated resulting in the formation of a very different product having different physical properties including improved ability to plasticize polyvinyl chloride. While tetralin alone initially yields phenyltetralylbutane which is subsequently converted into octahydroanthracene, octahydrophenanthrene, diphenylbutane and benzene, an equimolar mixture of tetralin and naphthalene gives hydrogenated binaphthyls as the predominate hydrodimer type along with lesser amounts of phenylnaphthylbutane and only minor amounts of phenyltetralylbutane. Table I provides a detailed description of how the nature of the components of the hydrodimer fraction depends on the type of aromatic substrate with which the tetralin is reacted. Furthermore, the tendency of the intially formed hydrodimers to react further and yield low molecular weight disproportionation products is significantly diminished when a mixture of naphthalene and tetralin is the reactant. This latter effect is still more pronounced when 1- or 2-methylnaphthalene or the mixture of mono- di- and trimethylnaphthalenes in certain selected aromatic-rich petroleum refinery streams are used instead of naphthalene, as shown by the data in Table II.

TABLE II

OVERALL CONVERSION AND SELECTIVITIES TO MAJOR PRODUCT FRACTIONS IN THE REACTION OF TETRALIN WITH VARIOUS AROMATIC SUBSTRATES AT 125° C. WITH 2 WT. PERCENT AlCl3 (IN MOLE PERCENT BY GAS CHROMATOGRAPHY)

| | | Selectivity To: | | |
|---|---|---|---|---|
| Substrate | Conversion | Hydrodimers | Disproportionation Products | High Mol. Wt. Products |
| Tetralin Alone | 27.7 | 37.2 | 59.5 | 3.3 |
| Tetralin With: | | | | |
| Naphthalene | 26.6 | 70.5 | 13.5 | 16.0 |
| 1-Methylnaphthalene | 21.8 | 78.2 | 11.0 | 10.8 |
| 2-Methylnaphthalene | 17.7 | 86.0 | 6.7 | 7.3 |
| Refinery Stream "A" | 14.9 | 94.0 | 4.0 | 2.0 |
| Refinery Stream "B" | 9.4 | 100.0 | nil | nil |

When methylnaphthalenes and/or methyltetralins are used as feedstocks the methyl groups become distributed over all the rings of the products as a result of transalkylation and hydrogen transfer processes. Because of these concurrent reactions, alkylnaphthalenes The process of the invention is readily carried out under relatively mild temperature conditions, preferably at the reflux temperature of the hydrocarbon mixture being used. Such temperature will range from about 200° to about 350° C. Most preferably, the reaction is carried out simply by refluxing the vapors of the hydrocarbon mixture over a bed of the acid catalyst. In this way the reactants and products have minimal contact with the acid and the product becomes concentrated in the container in which the reaction mixture is heated. The product in the container may be distilled to remove any lower boiling unreacted starting materials and the higher boiling product mixture of hydrodimers thereby obtained. Another alternative procedure of operation is to carry out the reaction in the vapor phase by simply passing vapors of the reactants over the catalyst.

The naphthalene hydrodimer mixtures which are produced by the process of this invention exhibit a surprisingly good compatibility with polyvinyl chloride resins and also have reasonable plasticization efficiency. This combination permits these products not only to be used at high replacement levels (i.e., from about 50% to about 90%) as secondary plasticizers, but even to be used as primary plasticizers. Because these products are made from low-value refinery streams by simple processing operations, they are less expensive to produce than conventional ester plasticizers such as di(2-ethylhexyl) phthalate, for example and, while they are less efficient than ester plasticizers, they are sufficiently less expensive to render them cost-effective as partial replacements or substitutes for ester plasticizers.

EXAMPLE 1

Preparation of HCP-300 (tetralin and naphthalene)

A mixture of 2563 g. (20.0 moles) of naphthalene and 2644 g. (20.0 moles) of tetralin was charged to the pot of a straight-through (non-siphoning) extraction apparatus. In the thimble of the extractor was placed 165 g. of Linde LZ-Y82 "Y" type zeolite catalyst in 1/16"×⅛" extrudate form. The hydrocarbon mixture was refluxed so that the refluxing naphthalene and tetralin trickled through the catalyst bed heated by the rising vapors. The mixture was refluxed until a conversion of approximately 85 percent was achieved. This was indicated by an increase in the pot temperature from the original 210° to about 300° C. Periodic gas chromatographic analysis of the pot contents was also used to monitor the conversion level.

Distillation of the product in a 20-plate Oldershaw column at atmospheric pressure removed the unreacted naphthalene and tetralin and a small amount of low molecular weight by-products. The main product, amounting to 3082 g., was distilled at 1 mm of Hg over the range of 180° to 200° C. The molecular weights of the components of this naphthalene hydrodimer product fall in the range of 252 to 272 according to a low ionizing voltage mass spectrogram.

EXAMPLE 2

Preparation of HCP-400 (tetralin and Sure Sol ®-180; a mixture of at least 80% by weight of methylnaphthalenes and the remainder comprising alkylbenzenes, indanes and biphenyls)

A mixture of 2842 g. of a refinery stream concentrate comprising about 80 percent mono-, di- and trimethylnaphthalene isomers and about 20 percent of other alkylaromatic hydrocarbons with 2644 g. of tetralin was reacted over Linde LZ-Y82 catalyst in the same manner as the above example. The 85–90 percent converted mixture was distilled to yield 2750 g. of a methylated naphthalene hydrodimer product boiling in the range of 190° to 250° C. @1 mm of Hg. The molecular weights of the components of this product fall in the range of 252 to 314.

The hydrodimer products of the process of the invention are viscous, water white, light yellow or amber colored liquids which boil over a range of from about 170° to about 220° C. at 1 mm Hg. These products are readily incorporated into PVC by milling it into sheets of the resin in accord with conventional procedures.

The attached tables provide data on the properties of poly(vinyl chloride) sheets compounded with varying levels of di(2-ethylhexyl) phthalate and two different hydrocarbon mixtures of the invention.

Summary of Tensile Data for HCP-300 Replacement of DOP

| Total Plasticizer (PHR) | % DOP Replaced | Tensile Strength Initial | Tensile Strength Aged | % Elongation Initial | % Elongation Aged | Modulus Initial | @ 100% Elong. Aged |
|---|---|---|---|---|---|---|---|
| 30 | 0 | 2825 | 3025 | 250 | 200 | 2525 | 2800 |
|  |  | 2825 | 2975 | 275 | 200 | 2450 | 2750 |
|  |  | 2925 | 2950 | 275 | 200 | 2550 | 2675 |
|  |  | 2900 | 3025 | 300 | 200 | 2425 | 2825 |
| 38 | 21 | 2875 | 2775 | 300 | 250 | 2200 | 2350 |
|  |  | 3000 | 2825 | 300 | 275 | 2250 | 2350 |
|  |  | 3075 | 2975 | 300 | 275 | 2250 | 2550 |
|  |  | 2950 | 2775 | 250 | 275 | 2250 | 2300 |
| 50 | 0 | 2500 | 2525 | 300 | 300 | 1400 | 1650 |
|  |  | 2575 | 2375 | 300 | 300 | 1450 | 1500 |
|  |  | 2575 | 2400 | 350 | 300 | 1350 | 1500 |
|  |  | 2575 | 2425 | 325 | 325 | 1400 | 1425 |
| 50 | 40 | 2775 | 2600 | 375 | 250 | 1600 | 1875 |
|  |  | 2850 | 2625 | 375 | 250 | 1600 | 2000 |
|  |  | 2725 | 2775 | 375 | 300 | 1575 | 1950 |
|  |  | 2800 | 2725 | 350 | 275 | 1575 | 2000 |
| 60 | 50 | 2400 | 2500 | 300 | 300 | 1175 | 1550 |
|  |  | 2425 | 2500 | 325 | 300 | 1300 | 1575 |
|  |  | 2450 | 2525 | 350 | 300 | 1200 | 1650 |
|  |  | 2575 | 2475 | 375 | 275 | 1200 | 1600 |
| 70 | 0 | 2125 | 1975 | 475 | 475 | 750 | 800 |
|  |  | 2125 | 1850 | 450 | 475 | 825 | 750 |
|  |  | 2125 | 1975 | 475 | 450 | 775 | 800 |
|  |  | 2075 | 1950 | 450 | 450 | 750 | 800 |
| 70 | 20 | 1950 | 2250 | 350 | 400 | 875 | 1150 |
|  |  | 2200 | 2175 | 450 | 400 | 800 | 950 |
|  |  | 2225 | 2150 | 450 | 400 | 825 | 1000 |
|  |  | 2300 | 2200 | 450 | 450 | 825 | 875 |
| 70 | 40 | 2350 | 2300 | 400 | 350 | 975 | 1175 |
|  |  | 2300 | 2225 | 400 | 350 | 850 | 1100 |
|  |  | 2300 | 2275 | 400 | 375 | 975 | 1100 |
|  |  | 2200 | 2175 | 400 | 350 | 900 | 1025 |
| 70 | 57.1 | 2350 | 2325 | 400 | 300 | 1050 | 1325 |
|  |  | 2500 | 2250 | 400 | 300 | 1175 | 1200 |
|  |  | 2475 | 2250 | 400 | 300 | 1075 | 1250 |
|  |  | 2475 | 2350 | 400 | 325 | 1050 | 1150 |
| 70 | 70 | 2400 | — | 425 | — | 1000 | — |
|  |  | 2525 | 2275 | 400 | 325 | 1150 | 1225 |
|  |  | 2525 | 2150 | 425 | 300 | 1175 | 1100 |
|  |  | 2450 | 2250 | 375 | 300 | 1100 | 1300 |
| 70 | 80 | 2525 | 2400 | 400 | 200 | 1325 | 1800 |
|  |  | 2525 | 2400 | 400 | 275 | 1300 | 1550 |
|  |  | 2575 | 2350 | 400 | 250 | 1325 | 1550 |
|  |  | 2525 | 2475 | 375 | 300 | 1300 | 1550 |
| 70 | 90 | 2425 | 2200 | 350 | 200 | 1300 | 1850 |
|  |  | 2450 | 2325 | 375 | 300 | 1275 | 1500 |
|  |  | 2400 | 2275 | 375 | 250 | 1350 | 1550 |
|  |  | 2400 | 2325 | 350 | 250 | 1350 | 1600 |
| 70 | 100 | 2400 | 2000 | 375 | 100 | 1300 | 2000 |
|  |  | 2425 | 2200 | 375 | 150 | 1450 | 1900 |
|  |  | 2450 | 2275 | 350 | 175 | 1550 | 1950 |
|  |  | 2450 | 2350 | 350 | 150 | 1550 | 2075 |
| 80 | 62.5 | 2225 | 2025 | 400 | 225 | 875 | 1150 |
|  |  | 2325 | 2125 | 425 | 325 | 925 | 1075 |
|  |  | 2200 | 2100 | 375 | 350 | 925 | 1000 |
|  |  | 2300 | 2075 | 400 | 325 | 925 | 1100 |

| Total Plasticizer (PHR) | % DOP Replaced | Initial Tensile | Initial % Elongation | Initial Modulus |
|---|---|---|---|---|
| 50 | 0 | 2200 | 375 | 1175 |
|  |  | 2100 | 350 | 1175 |
|  |  | 2150 | 375 | 1150 |
|  |  | 2175 | 400 | 1050 |
| 50 | 20 | 2350 | 350 | 1400 |
|  |  | 2250 | 350 | 1300 |
|  |  | 2925 | 350 | 1625 |
|  |  | 2700 | 325 | 1550 |
| 50 | 40 | 3125 | 350 | 1775 |
|  |  | 2950 | 375 | 1750 |
|  |  | 3000 | 375 | 1800 |
| 50 | 60 | 3175 | 325 | 2275 |
|  |  | 3100 | 300 | 2250 |
|  |  | 3100 | 275 | 2225 |
| 50 | 80 | 3175 | 300 | 2550 |
|  |  | 3175 | 300 | 2525 |
|  |  | 3150 | 275 | 2570 |
|  |  | 3075 | 2 5 | 2550 |
| 50 | 100 | 3225 | 250 | 2975 |
|  |  | 3225 | 225 | 3050 |
|  |  | 3000 | 300 | 2875 |
|  |  | 3000 | 300 | 2900 |
| 40 | 0 | 3125 | 325 | 1950 |
|  |  | 3050 | 300 | 2050 |
|  |  | 2900 | 300 | 2050 |
| 40 | 100 | 3650 | 200 | 3650 |
|  |  | 3850 | 225 | 2850 |
|  |  | 3600 | 250 | 3600 |
| 30 | 0 | 3700 | 275 | 3100 |
|  |  | 3625 | 300 | 2950 |
|  |  | 3675 | 275 | 3000 |

| Plasticizer (PHR) | % DOP Replaced | Hardness Initial | Hardness Aged | Volatility (%) |
|---|---|---|---|---|
| 30 | 0 | 91.6 | 75.3 | 0.28 |
| 30 | 100 | — | 85 | 2.62 |
| 38 | 21 | 92.3 | 88.0 | 1.09 |
| 40 | 0 | 81.0 | 78.0 | 0.23 |
| 40 | 100 | 94.7 | 86.7 | 3.40 |
| 50 | 0 | 76.5 | 74.7 | 1.49 |
| 50 | 20 | 76.3 | 75.7 | 1.98 |
| 50 | 40 | 77.2 | 72.5 | 3.54 |
| 50 | 60 | 82.6 | 69.7 | 2.27 |
| 50 | 80 | 85.3 | 83.0 | 2.16 |
| 50 | 100 | 92.0 | 93.0 | 3.04 |
| 60 | 50 | 73.0 | 70.3 | 5.03 |
| 70 | 0 | 66.3 | 65.0 | 1.75 |
| 70 | 20 | 65.3 | 66.7 | 3.25 |

-continued
Summary of Tensile Data for HCP-300 Replacement of DOP

| | | | | |
|---|---|---|---|---|
| 70 | 40 | 65.3 | 69.3 | 4.58 |
| 70 | 57.1 | 68.7 | 70.3 | 5.50 |
| 70 | 70 | 69.8 | 73.2 | 6.93 |
| 70 | 80 | 71.0 | 76.3 | 6.29 |
| 70 | 90 | 71.0 | 74.5 | 6.14 |
| 70 | 100 | 76.5 | 79.0 | 6.75 |
| 80 | 62.5 | 65.0 | 66.3 | 4.92 |

| Total Plasticizer (PHR) | % DOP Replaced | Tensile Initial | Strength Aged | % Elongation Initial | Aged | Modulus Initial | @ 100% Elong. Aged |
|---|---|---|---|---|---|---|---|
| 30 | 0 | 3325 | | 250 | | 2825 | |
|  |  | 3350 | | 300 | | 2750 | |
|  |  | 3150 | | 275 | | 2525 | |
| 38 | 21 | 3150 | | 300 | | 2175 | |
|  |  | 3275 | | 350 | | 2175 | |
|  |  | 3175 | | 350 | | 2150 | |
| 50 | 0 | 2375 | | 275 | | 1375 | |
|  |  | 2375 | | 300 | | 1325 | |
|  |  | 2425 | | 300 | | 1375 | |
| 50 | 40 | 2925 | | 350 | | 1700 | |
|  |  | 2750 | | 300 | | 1650 | |
|  |  | 2850 | | 300 | | 1650 | |
| 60 | 50 | 2800 | | 400 | | 1275 | |
|  |  | 2650 | | 350 | | 1350 | |
|  |  | 2750 | | 375 | | 1300 | |
| 70 | 0 | 1700 | | 375 | | 675 | |
|  |  | 2000 | | 400 | | 775 | |
|  |  | 2025 | | 400 | | 800 | |
| 70 | 20 | 2275 | | 400 | | 900 | |
|  |  | 2350 | | 400 | | 950 | |
|  |  | 2275 | | 350 | | 950 | |
| 70 | 40 | 2375 | | 350 | | 875 | |
|  |  | 2350 | | 350 | | 1025 | |
|  |  | 2350 | | 325 | | 1000 | |
| 70 | 57.1 | 2525 | | 375 | | 1100 | |
|  |  | 2575 | | 400 | | 1100 | |
|  |  | 2450 | | 350 | | 1100 | |
| 70 | 70 | 2575 | | 425 | | 1125 | |
|  |  | 2400 | | 350 | | 1175 | |
|  |  | 2550 | | 400 | | 1175 | |
| 70 | 80 | 2550 | | 400 | | 1275 | |
|  |  | 2700 | | 375 | | 1400 | |
|  |  | 2600 | | 400 | | 1275 | |
| 70 | 90 | 2550 | | 375 | | 1425 | |
|  |  | 2500 | | 350 | | 1350 | |
|  |  | 2550 | | 400 | | 1275 | |
| 70 | 100 | 2600 | | 375 | | 1725 | |
|  |  | 2575 | | 350 | | 1650 | |
|  |  | 2550 | | 300 | | 1650 | |

The above data is best evaluated by reference to the graphic displays of FIG. 1, FIG. 2, FIG. 3 and FIG. 4.

These figures provide a graphic display of the way the key tensile properties (ultimate tensile strength, elongation at break and tensile modulus at 100 percent elongation) are distributed over a broad range of PVC formulations incorporating the naphthalene hydrodimer mixture as hydrocarbon plasticizers. Data is given for PVC plasticized with DOP in which amounts of the DOP varying from 0 to 100 percent have been replaced by the compositions of this invention and for amounts of total plasticizer (combined DOP and compositions of the invention) varying from 30 to 80 parts per hundred parts by weight of PVC resin. Thus, the data at 70 PHR and 60 percent replacement are for a formulation containing 100 parts PVC resin, 28 parts DOP and 42 parts of the compositions of the invention. As long as the plasticizer remains fully compatible with the resin at the level used, the tensile modulus at 100 percent elongation (FIGS. 1 and 3) provides a good indication of the plasticization efficiency of the plasticizer; the lower the value at a given loading, the softer and more flexible is the formulation. By comparing the values for formulations plasticized by DOP alone (0 percent replacement) with those of formulations containing the compositions of the invention, it is seen that the values increase steadily as the amount of DOP replaced by the compositions of the invention increases. This shows that DOP is the more efficient plasticizer. However, the rather small increases in tensile modulus as shown by the numbers in the boxes (especially at replacements below 50 percent) indicates that the plasticization efficiency of the compositions of the invention are not notably inferior to that of DOP.

Figure 2:
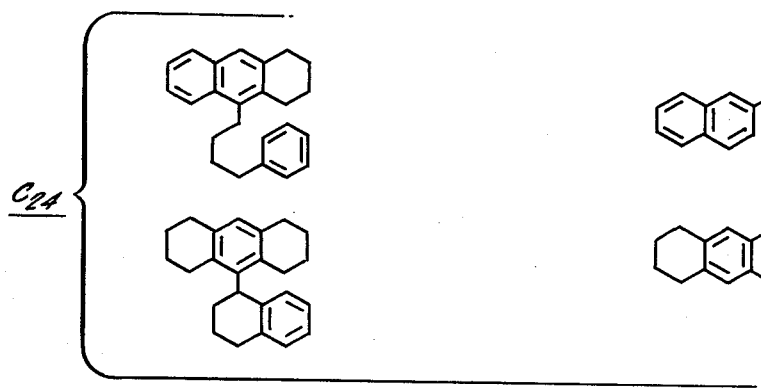
FIG. 2 lists structures for the secondary naphthalene hydrodimer types.
Figure 2:
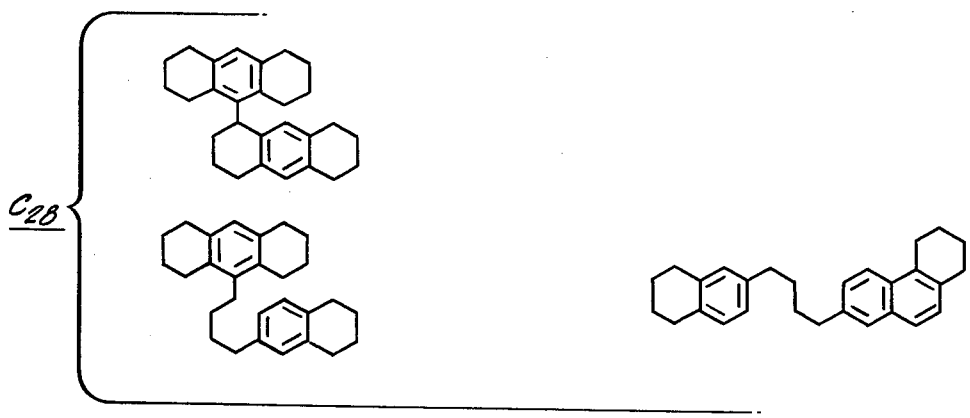
Figure 2:
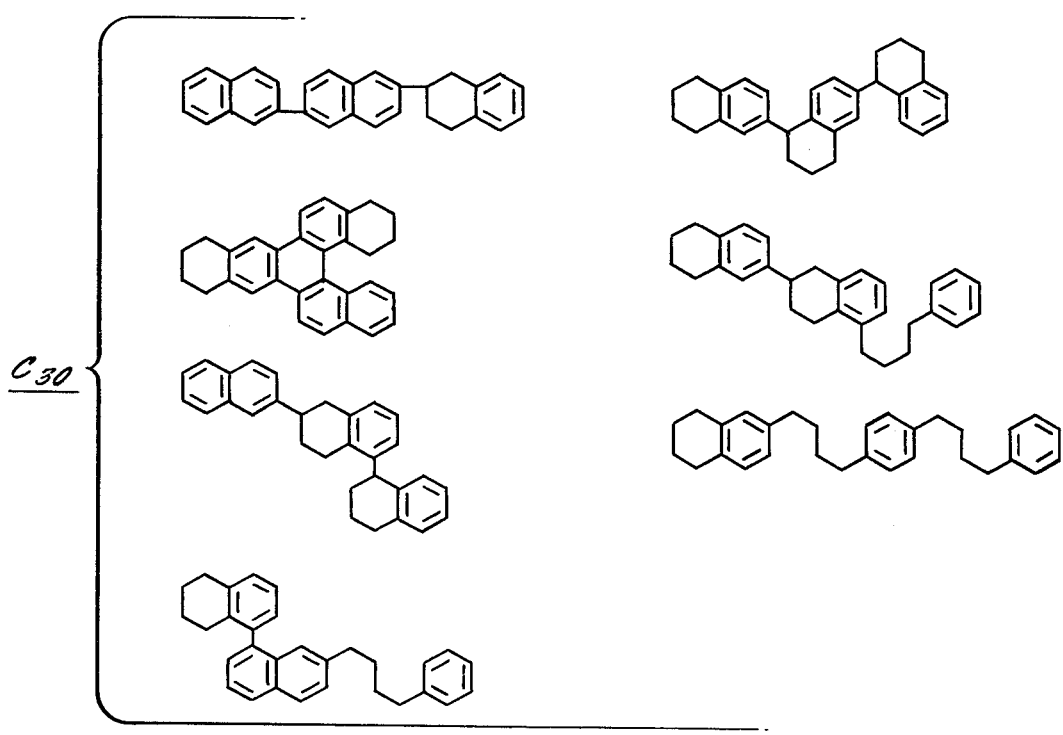

FIGS. 2 and 4 display the tensile strength and elongation at break of the same PVC formulations represented in FIGS. 1 and 3. The constancy of these values over the total range of replacement of DOP by the products of this invention is good indication of the compatibility of the products of the invention, and their mixture, with DOP with PVC resin in these formulations and other more qualitative tests corroborate the good efficiency of the products of the invention as a PVC plasticizer. Thus, the appearance, feel, lack of color, and other general qualitative properties all establish the good compatibility and plastization efficiency of the products of the invention for PVC.

I claim:

1. A process for making naphthalene hydrodimer mixtures which comprises reacting approximately equimolar amounts of a hydronaphthalene and naphthalene or an alkylnaphthalene with a strong acid catalyst at temperature between about 200° and about 350° C.

2. The process of claim 1 where the hydronaphthalene is tetralin.

3. The process of claim 1 wherein the reactants are tetralin and naphthalene.

4. The process of claim 1 wherein the reactants are tetralin and 1-methylnaphthalene.

5. The process of claim 1 wherein the reactants are a mixture of alkyltetralins and alkylnaphthalenes.

6. The process of claims 1, 2, 3, 4 or 5 where the catalyst is an acidic zeolite catalyst.

7. A naphthalene hydrodimer mixture useful as a plasticizer obtained by reacting approximately equimolar amounts of a hydronaphthalene and naphthalene or an alkylnaphthalene with a strong acid catalyst at a temperature between about 200° and about 350° C.

8. The mixture of claim 7 obtained from tetralin and naphthalene.

9. The hydrodimer mixture of claim 8 obtained from tetralin and 1-methylnaphthalene.

10. The hydrodimer mixture of claim 8 where the reactant mixture is obtained from a mixture of alkyltetralins and alkylnaphthalenes.

11. The hydrodimer mixture of claims 7, 8, 9, or 10 where the acid catalyst is an acidic zeolite.

12. A polyvinylchloride composition containing a plasticizing amount of a naphthalene hydrodimer mixture obtained by reacting approximately equimolar amounts of a hydronaphthalene and naphthalene or an alkylnaphthalene with a strong acid catalyst at a temperature of from about 200° to about 350° C.

13. The composition of claim 12 wherein the hydrodimer mixture is obtained from tetralin and naphthalene.

14. The composition of claim 12 wherein the hydrodimer mixture is obtained from tetralin and 1-methylnaphthalene.

15. The composition of claim 12 wherein the hydrodimer mixture is obtained from a mixture of alkyltetralins and alkylnaphthalenes.

16. The composition of claims 12, 13, 14 or 15 where the acid catalyst is an acidic zeolite.

* * * * *